United States Patent [19]

Preston

[11] Patent Number: 5,741,953
[45] Date of Patent: Apr. 21, 1998

[54] USE OF REACTIVE DISTILLATION IN THE MANUFACTURE OF METHYL TERTIARY BUTYL ETHER

[75] Inventor: Kyle Lee Preston, Port Arthur, Tex.

[73] Assignee: Huntsman Specialty Chemicals Corporation, Austin, Tex.

[21] Appl. No.: 516,039

[22] Filed: Aug. 17, 1995

[51] Int. Cl.$^6$ ........................................... C07C 41/34
[52] U.S. Cl. ..................... 568/699; 568/697; 568/698
[58] Field of Search .................... 568/697, 698, 568/699

[56] References Cited

U.S. PATENT DOCUMENTS 5,243,091  9/1993  Kruse et al. ........................... 568/697

Primary Examiner—Marianne M. Cintins
Assistant Examiner—Dwayne C. Jones
Attorney, Agent, or Firm—Russell R. Stolle; Ron D. Brown; Carl G. Ries

[57] ABSTRACT

An aqueous methanol feed stream contaminated with tertiary butyl alcohol is charged to a reactive distillation column having a reaction distillation section in the upper portion thereof containing an acid cation exchange resin and separated therein into a substantially anhydrous lower boiling methanol fraction contaminated with isobutylene and a higher boiling water fraction by charging the feed stream to the lower portion of the reactive distillation column to separate the feed stream into a higher boiling water fraction and a lower boiling methanol fraction containing a tertiary butyl alcohol-water azeotrope for upward flow into the reactive distillation section for reaction of the tertiary butyl alcohol to form isobutylene, MTBE and water and recovery of a substantially anhydrous lower boiling methanol fraction contaminated with isobutylene and MTBE.

5 Claims, 1 Drawing Sheet

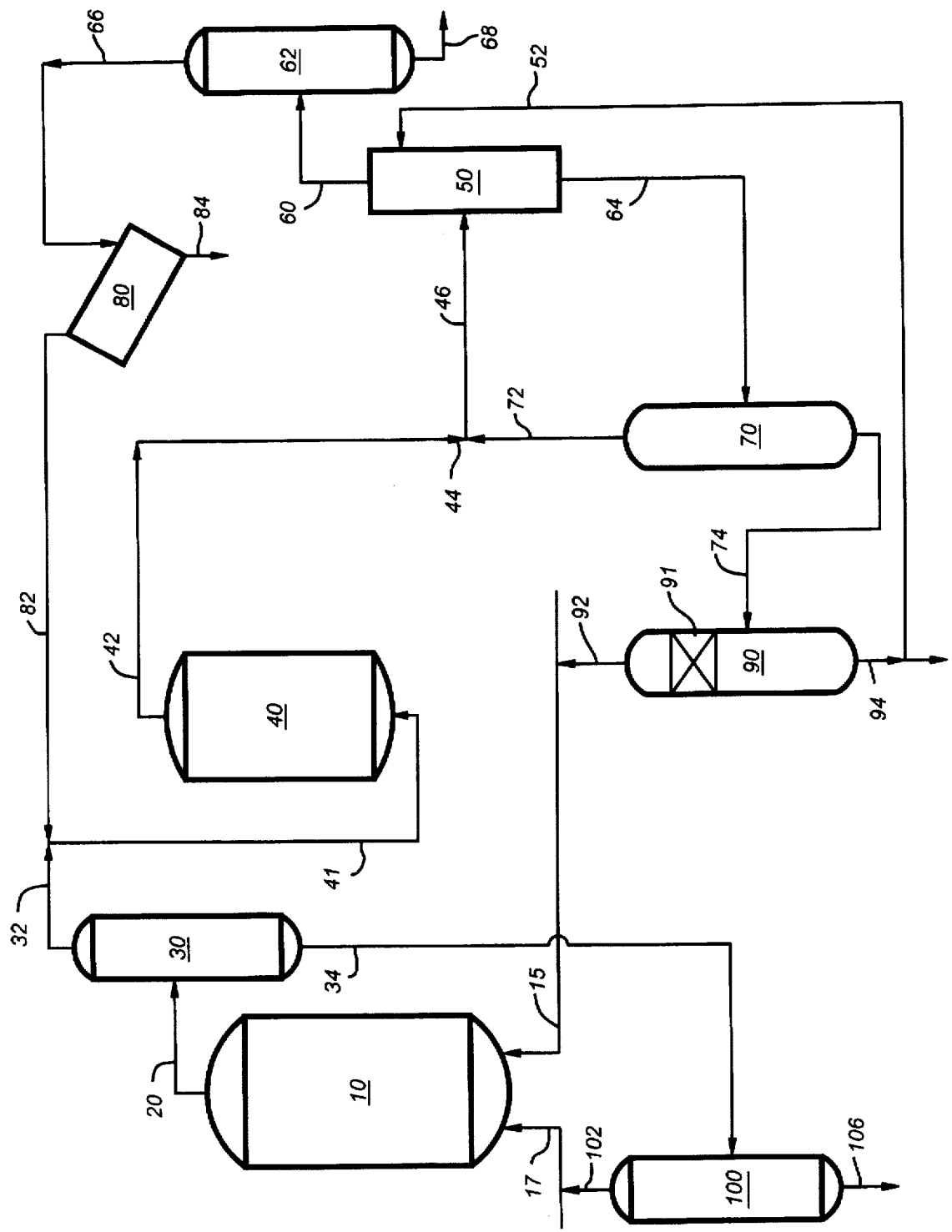

1

USE OF REACTIVE DISTILLATION IN THE MANUFACTURE OF METHYL TERTIARY BUTYL ETHER

BACKGROUND OF THE INVENTION

1. Technical Field of the Invention

This invention relates to the reactive distillation of MeOH contaminated with TBA and water in order to convert the TBA to isobutylene to obtain a substantially anhydrous MeOH stream contaminated with isobutylene (IBTE). More particularly, this invention relates to a process for the manufacture of methyl tertiary butyl ether (MTBE) from tertiary butyl alcohol (TBA) and methanol (MeOH) wherein methanol is recycled. Still more particularly, this invention relates to a process for the manufacture of MTBE from TBA and MeOH wherein by-product isobutylene formed by the reaction of TBA with MeOH in a primary reactor is reacted with excess MeOH in a finishing reactor to provide a finishing reactor product comprising MTBE, unreacted MeOH, unreacted isobutylene and by-product TBA and water and wherein contaminating quantities of TBA and water are removed from MeOH to be recycled to the primary reactor.

In particular, this invention relates to a process for the manufacture of methyl tertiary butyl ether (MTBE) in a primary reactor from tertiary butyl alcohol (TBA) and methanol (MeOH), wherein TBA formed in a finishing reactor by the reaction of by-product isobutylene with water is recovered together with water and MeOH from the finishing reactor product and subjected to reactive distillation to provide substantially anhydrous MeOH contaminated with IBTE for recycle to the primary reactor.

2. Prior Art

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

Kruse et al. U. S. Pat. No. 5,243,091 discloses a method for the preparation of methyl tertiary butyl ether wherein a mixture of methanol and tertiary butyl alcohol is catalytically reacted to form a reaction product that is separated into a first lighter distillation fraction comprising isobutylene, methanol and methyl tertiary butyl ether and a first heavier distillation fraction comprising methanol, tertiary butyl alcohol and water. The first heavier distillation fraction is distilled to provide a second lighter TBA fraction for recycle. The first lighter distillation fraction and isobutylene are reacted in a finishing reactor to form a finishing reactor conversion product that is charged to a methanol extraction zone and countercurrently contacted with water to provide an overhead extract comprising MTBE, water and isobutylene, from which the isobutylene is recovered for recycle.

Gupta U.S. Pat. No. 5,292,964 discloses a method for the preparation of methyl tertiary butyl alcohol wherein a mixture of methanol and tertiary butyl alcohol are catalytically reacted to form a reaction product containing the water of etherification and at least one mol of methanol per two moles of methyl tertiary butyl ether, wherein the reaction product is fractionated to separate a lighter methanol and methyl tertiary butyl ether fraction from the water and tertiary butyl alcohol and wherein the methanol in the lighter distillation fraction is reacted with isobutylene to form additional methyl tertiary butyl ether.

Gupta states that it is essential to provide a reaction product containing at least one mol of methanol per two moles of methyl tertiary butyl ether, so that water is separable from the methyl tertiary butyl ether in the fractionating column to provide a lighter distillation fraction substantially free from water.

Smith U. S. Pat. No. 4,215,011 discloses a reactive distillation column having both a catalytic function and a distillation function that is useful, for example, in the polymerization of butene.

In Smith U.S. Pat. No. 4,232,177 method for conducting chemical reactions in a reactive distillation column is disclosed wherein a reaction mixture is fed to a reactive distillation column and contacted with a fixed bed catalytic packing to concurrently carry out the reaction and to fractionate the reaction mixture.

Various types of catalytic packing that can be used in a reactive distillation column are disclosed in Smith U.S. Pat. No. 4,443,559.

Smith U. S. Pat. No. 5,118,873 discloses a process wherein isobutylene and methanol are reacted in the presence of an acid cation exchange resin to form MTBE and concurrently fractionated to provide an overhead fraction comprising unreacted isobutylene and unreacted methanol and a bottoms fraction comprising methyl tertiary butyl ether and contaminants.

In Kruse et al. U. S. patent application entitled "Method for the Reduced Formation of Tertiary Butyl Alcohol in a Finishing Reactor in the Manufacture of Methyl Tertiary Butyl Ether" (Docket No. 81,256), now U.S. Pat. No. 5,387,721 a process is disclosed for the preparation of methyl tertiary butyl ether wherein a mixture of methanol and tertiary butyl alcohol are catalytically reacted to form a reaction product comprising unreacted methanol, unreacted tertiary butyl alcohol, water, isobutylene and methyl tertiary butyl ether; the reaction product being separated into a substantially anhydrous first lighter distillation fraction comprising isobutylene, methanol and methyl tertiary butyl ether and a second heavier distillation fraction comprising methanol, tertiary butyl alcohol and water, and the isobutylene and methanol in the first distillation fraction are reacted in a finishing reactor to form an isobutylene conversion product that contains additional methyl tertiary butyl ether and that is substantially free from tertiary butyl alcohol.

SUMMARY OF THE INVENTION

In accordance with the present invention, methanol contaminated with water and tertiary butyl alcohol is charged to a reactive distillation column having a reaction distillation section in the upper portion thereof containing an acid cation exchange resin. The contaminated methanol is separated into a higher boiling water fraction for withdrawal adjacent the bottom of the tower and a lower boiling fraction comprising methanol and a tertiary butyl alcohol-water azeotrope for upward flow into the reactive distillation section, where the tertiary butyl alcohol is dehydrated to provide a mixture of isobutylene, water and methanol. The water formed in the reactive distillation section will flow downwardly for recovery with the higher boiling water fraction and the methanol and isobutylene will flow upwardly through the reactive distillation section, for recovery as a substantially anhydrous lower boiling methanol fraction contaminated with isobutylene.

This invention relates to an improvement in a process for the manufacture of MTBE from TBA and MeOH wherein tertiary butyl alcohol and methanol are reacted in a primary reactor in the presence of an acid cation exchange resin to provide a primary reaction product comprising methyl tertiary butyl ether, unreacted tertiary butyl alcohol, unreacted methanol, isobutylene and water, wherein the primary reaction product is separated in a primary distillation column to provide a lower boiling primary distillation fraction comprising methyl tertiary butyl ether, isobutylene, unreacted methanol and water, and a higher boiling primary distillation fraction comprising methanol, tertiary butyl alcohol and water.

The lower boiling primary distillation fraction is charged to a finishing reactor where a significant portion of the isobutylene and a portion of the methanol are converted to methyl tertiary butyl ether and form a finishing reactor conversion product that will contain MTBE, isobutylene, methanol and contaminating quantities of tertiary butyl alcohol and water.

The finishing reactor conversion product is charged to a methanol solvent extraction zone and countercurrently contacted therein with water to provide an overhead raffinate comprising isobutylene, water and methyl tertiary butyl ether and an extract comprising methanol and contaminating quantities of tertiary butyl alcohol and water.

The raffinate is processed to provide isobutylene for recycle and a methyl tertiary butyl ether product.

A stream comprising methanol contaminated with tertiary butyl alcohol and water that is obtained from the raffinate is charged to a reactive distillation column having a reaction distillation section in the upper portion thereof and fractionated therein in the manner described above to convert the tertiary butyl alcohol to isobutylene and water to thereby provide a higher boiling water fraction for withdrawal adjacent the bottom of the tower and a substantially anhydrous lower boiling methanol fraction contaminated with isobutylene for recycle to the primary reactor.

In greater detail, this invention relates to an improvement in a process for the manufacture of MTBE from TBA and MeOH which comprises:

a) continuously passing a feed mixture comprising TBA and MeOH through a primary MTBE reactor containing a bed of a TBA/MeOH etherification catalyst under etherification reaction conditions to form an etherification reaction product comprising unreacted MeOH, unreacted TBA, water, isobutylene (IBTE) and MTBE, b) continuously charging the primary reaction product to a primary MTBE distillation zone and separating it therein into a first lighter primary distillation fraction comprising MTBE, IBTE, MeOH and water, c) continuously charging the first primary distillation fraction to a finishing reactor containing a solid resin IBTE/MeOH etherification catalyst and reacting the IBTE and MeOH to form a finishing reactor conversion product comprising MTBE, unreacted MeOH, unreacted IBTE, TBA and water, d) continuously charging the finishing reactor conversion product to a methanol solvent extraction zone and countercurrently contacting it therein with water to provide an overhead raffinate comprising IBTE and MTBE and an extract comprising MeOH and contaminating quantities of TBA and water, e) processing the raffinate to provide IBTE for recycle and a MTBE product stream, f) continuously charging the extract to a secondary MTBE distillation column and separating it therein into a lighter secondary distillation fraction comprising MTBE, and a heavier secondary distillation fraction comprising MeOH and contaminating quantities of TBA and water, g) continuously charging the heavier secondary distillation fraction to a reactive distillation column effective for the separation of the MeOH and TBA/water azeotrope from the water contained in the heavier secondary distillation fraction to thereby provide a higher boiling reactive distillation water fraction for withdrawal adjacent the bottom of the tower and a lower boiling fraction comprising MeOH and a tertiary butyl alcohol-water azeotrope for upward flow into the reactive distillation section for reaction of the TBA to IBTE, MTBE and water and for recovery of a the substantially anhydrous MeOH fraction contaminated with IBTE and MTBE for recycle to the primary reactor.

DETAILED DESCRIPTION OF THE PRESENT INVENTION

The Etherification Reaction Catalyst

In accordance with the MTBE manufacture and purification method of the present invention, a primary etherification reactor containing a bed of etherification catalyst is utilized. A wide variety of etherification catalysts can be used for this purpose, such as supported phosphorus acid-type catalysts. A preferred catalyst is an acid cation exchange resin such as a sulfonic acid resin etherification catalyst as exemplified by sulfonated polystyrene resins cross-linked with divinyl benzene.

Any suitable solid resin etherification catalyst may be used for this purpose, such as an acidic ion exchange resin consisting essentially of sulfonated polystyrene, for example, a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

Also, Kieselguhr impregnated with phosphoric acid as disclosed in Frolich U.S. Pat. No. 2,282,469, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc., may be used.

Zeolites as disclosed in Japanese Patent 0007432 or aluminosilicate zeolites as disclosed in Chang et al. U.S. Pat. No. 4,058,576 may also be used.

The reaction conditions to be utilized when reacting methanol with tertiary butyl alcohol in the presence of a sulfonic acid resin etherification catalyst of the type disclosed in the prior art include a reaction temperature of about 90° to about 140° C., a pressure of about 30 to about 500 psia and a space velocity of about 0.5 to about 20 volumes of feed per volume of etherification catalyst per hour.

The Finishing Reactor

In accordance with the present invention, a lower boiling primary distillation fraction is obtained during the recovery process, which contains both isobutylene and methanol. It is brought into contact with a solid resin etherification catalyst, as described above, in a finishing reactor in order to convert a significant portion of the isobutylene and methanol to methyl tertiary butyl ether.

The a lower boiling primary distillation fraction will normally contain from about 0.05 to about 0.2 wt. % of water, from about 5 to about 10 wt. % of isobutylene, from about 70 to about 80 wt. % of methyl tertiary butyl ether, and from about 10 to about 20 wt. % of methanol.

An isobutylene reaction mixture is prepared comprising the higher boiling primary distillation fraction and an isobutylene recycle fraction containing additionally about 1 to 10 wt. % of isobutylene, based on the weight of the higher boiling primary distillation fraction. Thus, the isobutylene reaction mixture may comprise from about 6 to about 15 wt. % of isobutylene, from about 65 to about 75 wt. % of methyl tertiary butyl ether and from about 10 to about 20 wt. % of methanol.

Any suitable solid resin etherification catalyst may be used in the finishing reactor for this purpose, such as an acidic ion exchange resin consisting essentially of sulfonated polystyrene, for example, a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalyst of this nature is disclosed, for example, in Rao U.S. Pat. No. 4,144,138.

The isobutylene reaction mixture is brought into contact with a solid resin etherification catalyst in the isobutylene conversion zone or finishing reactor under conversion conditions including, for example, a temperature of about 35° to about 130° C., a pressure of about 30 to about 500 psia and a contact time of about 0.5 to about 20 volumes of first primary distillate fraction per volume of etherification catalyst per hour. As a consequence, an isobutylene conversion product is formed which will normally contain from about 0 to about 10 wt. % of isobutylene, about 75 to about 85 wt. % of methyl tertiary butyl ether and from about 10 to about 15 wt. % of methanol and about 0.2 to about 2 wt. % of tertiary butyl alcohol.

BRIEF DESCRIPTION OF THE DRAWING

The drawing is a schematic flow sheet with conventional parts omitted showing the general reaction and recovery sequence of the present invention for the manufacture of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with the present invention, there is provided a primary etherification reactor 10 containing a bed of solid etherification catalyst.

A substantially peroxides-free tertiary butyl alcohol feed stream is continuously charged by a charge line 17 together with a recycle fraction 102 to primary reaction zone 10. Fresh methanol is continuously charged to the primary reactor 10 by a line 15, together with a recycle stream 92 containing recycle methanol and isobutylene. The flow of methanol and tertiary butyl alcohol to the primary reactor 10 is regulated so that a molar excess of methanol is present, such as, for example, a molar ratio of about 1.1 to about 3 moles of methanol per mol of tertiary butyl alcohol.

Within the primary reactor 10, the feed mixture is brought into contact with the bed of etherification catalyst, such as a sulfonic acid resin etherification catalyst under reaction conditions including a pressure of about 30 to about 500 psia, and more preferably from about 200 to about 300 psia, a temperature of about 30° to about 200° C., and more preferably from about 80° to about 140° C., and still more preferably from about 90° to about 130° C. When the catalyst is a supported phosphorus acid-type catalyst, the reaction temperature may suitably be in the range of about 150° to about 190° C.

Contact time within the primary reaction zone 10 is suitably such that about 0.5 to about 20 volumes of feed mixture per volume of etherification catalyst per hour are fed to the etherification reaction zone 10. More preferably from about 1 to about 4 volumes of feed mixture per volume of etherification catalyst per hour are used.

Within the primary reactor 10, methanol will react with the tertiary butyl alcohol to form methyl tertiary butyl ether and water which will be contained in a primary reaction product discharged from the primary reactor 10 by way of a line 20 leading to a primary methyl tertiary butyl ether (MTBE) distillation column 30.

As a specific example, when the solid etherification catalyst is a sulfonic acid resin such as Amberlyst 15 and when the molar ratio of methanol to tertiary butyl alcohol in the feed mixture charged to the primary reactor 10 is a ratio of about 2.0 moles of methanol per mole of tertiary butyl alcohol, and the reaction is conducted at a temperature of about 100° C. at a feed rate of about 2.0 volumes of feed mixture per volume of catalyst per hour, the primary etherification reaction product will typically have the composition in part shown by the following table:

| PRIMARY ETHERIFICATION REACTION PRODUCT | |
|---|---|
| Component | % |
| Water | 14.0 |
| Methanol | 27.6 |
| Isobutylene | 3.0 |
| TBA[1] | 14.1 |
| MTBE[2] | 34.5 |
| Other[3] | 6.8 |

[1]Tertiary butyl alcohol
[2]Methyl tertiary butyl ether
[3]Includes the acetone, propanol, and any ditertiary butyl peroxide, tertiary butyl formate, etc., initially present in the tertiary butyl alcohol feedstock.

The primary etherification reaction product charged to the primary MTBE distillation column 30 by way the charge line 20 is fractionated therein under distillation conditions including a liquid reflux temperature of about 30° to about 100° C., and more preferably about 40° to about 80° C., a reboiler temperature of about 80° to about 115° C. and more preferably from about 95° to about 105° C., and a pressure of about 15 to about 60 psia, the distillation conditions being selected such that substantially all of the MTBE in the etherification reaction product 20 is taken overhead from the first distillation column 30 by a line 32 and such that substantially all of the water exits the distillation column adjacent the bottom thereof by the line 34.

As a consequence, the primary distillation fraction 32 taken overhead from the distillation column 30 will contain substantially all of the isobutylene and substantially all of the methyl tertiary butyl ether, some water and part of the methanol charged to the primary distillation column 30. The primary heavier distillation fraction 34 discharged from the primary MTBE distillation column 30 will comprise methanol, tertiary butyl alcohol and water.

Typically, the lower boiling primary distillation fraction will contain from about 0.05 to about 1 wt. % of water, from about 5 to about 10 wt. % of isobutylene, from about 70 to about 80 wt. % of methyl tertiary butyl ether and from about 10 to about 20 wt. % of methanol.

The primary lower boiling distillation fraction 32 in admixture with recycle isobutylene added by a recycle line 82 is charged by way of charge line 41 to an isobutylene conversion zone, or finishing reactor 40 containing a bed of solid resin etherification catalyst such as a bed of Amberlyst 15 sulfonated polystyrene-divinyl benzene copolymer acidic ion exchange resin. Suitably, the admixture in the line 41 will contain about 2 to about 15 parts of recycle isobutylene per 100 parts of primary distillation fraction 32.

Etherification reaction conditions established in the finishing reactor 40 may include, for example, a temperature of about 35° to about 130° C., and more preferably from about 40° to about 70° C., a pressure of about 50 to about 500 psia, and more preferably from about 150 to about 250 psia, and a contact time of about 0.5 to about 4 volumes of primary distillation fraction per volume of solid resin etherification catalyst per hour. As a consequence, a portion of the methanol and isobutylene contained in the first distillation fraction 32 will be converted to methyl tertiary butyl ether. Typically, the conversion will amount to about 30 to about 60 wt. %, based on the isobutylene. Water present in the fraction 41 will react with isobutylene to form tertiary butyl alcohol.

The composition of a representative feedstock and a representative finishing reactor conversion product may be characterized as follows:

| ISOBUTYLENE FEEDSTOCK AND FINISHING REACTOR PRODUCT | | |
|---|---|---|
| Component | Feed, wt. % | Product, wt. % |
| Water | 0.01 wt. % | 0.4 wt. % |
| Methanol | 13.11 wt. % | 11.5 wt. % |
| Isobutylene | 12.47 wt. % | 1.8 wt. % |
| TBA | 0.00 wt. % | 1.0 wt. % |
| MTBE | 73.29 wt. % | 83.5 wt. % |

The finishing reactor conversion product is discharged from the finishing reactor 40 by a line 42 and is charged to a manifold 44 and thence via line 46 to a methanol solvent extraction zone 50 where it is countercurrently contacted with water introduced into the solvent extraction zone 50 by a charge line 52.

Within the methanol solvent extraction zone 50, solvent extraction conditions are established for countercurrent solvent extraction including a ratio of isobutylene to water within the range of about 0.8 to about 1.8 volumes of isobutylene per volume of water per hour, and more preferably a ratio of about 1.0 to about 1.5 volumes of isobutylene per volume of water. Extraction conditions may suitably include a temperature of about 20° to about 60° C., and more preferably from about 30° to about 40° C., and a pressure of about 50 to about 500 psia, and more preferably from about 50 to about 150 psia.

As a consequence, a supernatant raffinate will be formed which is withdrawn from the methanol solvent extraction zone 50 by line 60 leading to a second methyl tertiary butyl ether purification distillation column 62. The extract is discharged from the solvent extraction zone 50 by way of a bottoms charge line 64 leading to a third methyl tertiary butyl ether distillation column 70.

Within the second methyl tertiary butyl ether purification distillation column 62, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a lower boiling distillation fraction 66 discharged from the second distillation zone 62 and a higher boiling fourth distillation fraction 68 consisting essentially of product, namely methyl tertiary butyl ether.

The lower boiling distillation fraction 66 will comprise a mixture of isobutylene and water and is suitably charged to a decantation zone 80 where it can settle to form a supernatant isobutylene phase withdrawn from the decantation zone 80 by way of a line 82. Water is discharged in the decantation zone 80 by way of a water discharge line 84 and is suitably purged from the system.

The extract 64 charged to the third distillation zone 70 will comprise methyl tertiary butyl ether, tertiary butyl alcohol, methanol and water, and is suitably fractionated therein under distillation conditions including a liquid reflux temperature of about 30° to about 90° C., and more preferably from about 50° to about 75° C., and a reboiler temperature of about 80° to about 120° C., and more preferably from about 105° to about 115° C., and a pressure of about 15 to about 60 psia, and more preferably from about 40 to about 50 psia, to form a fifth lighter distillation fraction 72 comprising methyl tertiary butyl ether which may suitably be charged to the manifold 44 for the charge line 46 to the methanol solvent extraction zone 50. A higher boiling impure methanol distillation fraction comprising water, tertiary butyl alcohol and methanol is discharged from the third distillation column 70 by a line 74 leading to a reactive distillation column 90.

In accordance with the present invention, methanol contaminated with water and tertiary butyl alcohol is charged to a reactive distillation column 90 having a reaction distillation section 91 in the upper portion thereof containing an acid cation exchange resin. The contaminated methanol is separated into a higher boiling water fraction for withdrawal adjacent the bottom of the tower and a lower boiling fraction comprising methanol and a tertiary butyl alcohol-water azeotrope is formed and flows upwardly into the reactive distillation section, where the tertiary butyl alcohol is reacted to provide a mixture of isobutylene, MTBE, water and methanol. The water formed in the reactive distillation section will flow downwardly for recovery with the higher boiling water fraction and the methanol, MTBE and isobutylene will flow upwardly through the reactive distillation zone, for recovery as the substantially anhydrous higher boiling methanol fraction contaminated with isobutylene and MTBE.

Distillation conditions that may used in the reactive distillation column 90 may suitably include a liquid reflux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia.

A lower boiling distillation fraction 92 is discharged from reactive distillation column 90 which may be suitably charged to the line 15 for recycle to the etherification reaction zone 10. A higher boiling distillation fraction consisting essentially of water is discharged from the reactive distillation column 90 by way of a line 94 and may be partially discharged from the system. The remainder of the water is recycled to the solvent extraction zone 50 by line 52.

The second distillation fraction 34 discharged from the first MTBE distillation zone 30 is charged to a fifth tertiary butyl alcohol recovery distillation zone 100 where it is fractionated under distillation conditions including a liquid reflux temperature of about 35° to about 170° C., and more preferably about 140° to about 150° C., and a reboiler temperature of about 100° to about 190° C., more preferably about 170° to about 180° C., and at a pressure of about 15 to about 190 psia, and more preferably about 110 to about 160 psia, into a lighter tertiary butyl alcohol recycle distillation fraction discharged in the fifth distillation zone 100 by a line 102 leading to tertiary butyl alcohol charge line 17 and a heavier water distillation fraction is discharged from the distillation zone 100 by a line 106.

Through the provision of the process of the present invention, the water content of the stream 15 is reduced. TBA cannot be completely separated from water by distillation because of a TBA/water azeotrope. By using reactive distillation in the distillation column 90, the TBA is converted to isobutylene, MTBE and water. Isobutylene, MTBE and methanol can be separated from water by distillation, thus reducing the amount of water recycled to the primary reactor 10 through the line 15, thereby increasing reactor conversion.

What is claimed is:

1. A method for the distillation of an aqueous methanol feed stream contaminated with tertiary butyl alcohol in a reactive distillation column having a reaction distillation section in the upper portion thereof containing an acid cation exchange resin which comprises:

charging an aqueous methanol feed stream contaminated with tertiary butyl alcohol to the lower portion of the reactive distillation column under distillation conditions effective for the separation of the methanol and tertiary butyl alcohol from the water contained in the feed stream to provide a higher boiling water fraction and a lower boiling methanol fraction containing a tertiary butyl alcohol-water azeotrope for upward flow into the reactive distillation section reacting the tertiary butyl alcohol flowing into the reactive distillation section to convert the tertiary butyl alcohol to isobutylene, MTBE and water and to provide a mixture of isobutylene, MTBE, methanol and water, and recovering a substantially anhydrous lower boiling methanol fraction contaminated with isobutylene and MTBE.

2. A process for the manufacture of MTBE from TBA and MeOH which comprises:

a) reacting TBA and MeOH in a primary reactor in the presence of an acid cation exchange resin to provide a primary reaction product comprising methyl tertiary butyl ether, TBA, MeOH, isobutylene, water and lower boiling impurities, b) separating the primary reaction product in a primary distillation column to provide a lower boiling primary distillation fraction comprising methyl tertiary butyl ether, isobutylene, unreacted methanol, and water, and a higher boiling primary distillation fraction comprising methanol, tertiary butyl alcohol and water, c) charging the lower boiling primary distillation fraction to a finishing reactor to convert isobutylene and methanol to methyl tertiary butyl ether and form a finishing reactor conversion product comprising MTBE, MeOH, isobutylene contaminating quantities of TBA and water;

d) charging the finishing reactor conversion product to a methanol solvent extraction zone and countercurrently contacting it therein with water to provide an overhead raffinate comprising isobutylene and methyl tertiary butyl ether and an extract comprising methyl tertiary butyl ether, methanol, tertiary butyl alcohol and water;

e) processing the extract to obtain a stream comprising methanol contaminated with tertiary butyl alcohol and water;

f) charging said stream to a reactive distillation column having a reaction distillation section in the upper portion thereof and fractionating said stream therein to convert the tertiary butyl alcohol to isobutylene, MTBE and water and to provide a mixture of isobutylene, MTBE, methanol and water and recovering a substantially anhydrous lower boiling methanol fraction contaminated with isobutylene and MTBE for withdrawal adjacent the top of said reactive distillation column for recycle to the primary reactor and a higher boiling water fraction for withdrawal adjacent the bottom of the reactive distillation column.

3. A method as in claim 2 wherein:

the reaction is conducted in the primary reactor at a reaction temperature of about 90° to about 140° C., a pressure of about 30 to about 500 psia and a space velocity of about 0.5 to about 20 volumes of feed per volume of etherification catalyst per hour, and the reaction is conducted in the finishing reactor at a reaction temperature of about 35° to about 130° C., a pressure of about 30 to about 500 psia and a space velocity of about 0.5 to about 20 volumes of feed per volume of etherification catalyst per hour.

4. A process for the manufacture of MTBE from TBA and MeOH which comprises:

a) reacting TBA and MeOH in a primary reactor in the presence of an acid cation exchange resin at a reaction temperature of about 90° to about 140° C., a pressure of about 30 to about 500 psia and a space velocity of about 0.5 to about 20 volumes of feed per volume of etherification catalyst per hour to provide a primary reaction product comprising methyl tertiary butyl ether, TBA, MeOH, isobutylene, water and lower boiling impurities, b) distilling the primary reaction product in a primary distillation column to provide a lower boiling primary distillation fraction comprising methyl tertiary butyl ether, isobutylene, unreacted methanol, and water, and a higher boiling primary distillation fraction comprising methanol, tertiary butyl alcohol and water.

c) charging the lower boiling primary distillation fraction to a finishing reactor containing a bed of a cation ion exchange resin conversion catalyst for reaction at a reaction temperature of about 35° to about 130° C., a pressure of about 30 to about 500 psia and a space velocity of about 0.5 to about 20 volumes of feed per volume of etherification catalyst per hour to convert isobutylene and methanol to methyl tertiary butyl ether and form a finishing reactor conversion product comprising MTBE, MeOH, isobutylene containing contaminating quantities of TBA and water;

d) charging the finishing reactor conversion product to a methanol solvent extraction zone and countercurrently contacting it therein with water to provide an overhead raffinate comprising isobutylene and methyl tertiary butyl ether and an extract comprising methyl tertiary butyl ether, methanol, tertiary butyl alcohol and water;

e) charging the extract to a second methyl tertiary butyl ether distillation column and separating it therein into a lower boiling methyl tertiary butyl ether fraction and a higher boiling impure methanol fraction contaminated with tertiary butyl alcohol and water.

f) charging said stream to a reactive distillation column having a reaction distillation section in the upper portion thereof and fractionating said stream therein to convert the tertiary butyl alcohol to isobutylene, MTBE and water and to provide a mixture of isobutylene, MTBE, methanol and water and recovering a substantially anhydrous lower boiling methanol fraction contaminated with isobutylene and MTBE for withdrawal adjacent the top of said reactive distillation column for recycle to the primary reactor and a higher boiling water fraction for withdrawal adjacent the bottom of the reactive distillation column.

5. A method as in claim 4 wherein the raffinate is charged to a methyl tertiary butyl ether distillation column and separated therein into a lower boiling fraction comprising isobutylene and water and a higher boiling methyl tertiary butyl ether product fraction and wherein the lower boiling fraction is charged to a decantation zone and separated therein into a water fraction and a recycle isobutylene fraction.

* * * * *